(12) United States Patent
Chabot et al.

(10) Patent No.: US 12,140,604 B2
(45) Date of Patent: *Nov. 12, 2024

(54) SYSTEM AND METHOD FOR MEASURING BRIX OF A LIQUID

(71) Applicant: Les Equipements D'Erabliere C.D.L. Inc, Saint-Lazare (CA)

(72) Inventors: Marc-Andre Chabot, Saint-Damien-de-Buckland (CA); Martin Chabot, Sainte-Claire (CA)

(73) Assignee: Les Equipements D'Erabliere C.D.L. Inc, Saint-Lazare (CA)

( * ) Notice: Subject to any disclaimer, the term of this patent is extended or adjusted under 35 U.S.C. 154(b) by 213 days.

This patent is subject to a terminal disclaimer.

(21) Appl. No.: 17/668,854

(22) Filed: Feb. 10, 2022

(65) Prior Publication Data
US 2022/0252491 A1    Aug. 11, 2022

Related U.S. Application Data

(60) Provisional application No. 63/147,820, filed on Feb. 10, 2021.

(51) Int. Cl.
| | |
|---|---|
| *G01N 5/00* | (2006.01) |
| *G01F 22/00* | (2006.01) |
| *G01K 13/02* | (2021.01) |
| *G01N 1/38* | (2006.01) |
| *G01N 33/02* | (2006.01) |

(52) U.S. Cl.
CPC ............... *G01N 5/00* (2013.01); *G01F 22/00* (2013.01); *G01K 13/026* (2021.01); *G01N 1/38* (2013.01)

(58) Field of Classification Search
CPC . G01N 5/00; G01N 1/38; G01N 33/02; G01F 22/00; G01K 13/026; A23V 2002/00; A23L 2/60
See application file for complete search history.

(56) References Cited

U.S. PATENT DOCUMENTS

2012/0232471 A1* 9/2012 Chen .................... A61M 1/1607
604/82

FOREIGN PATENT DOCUMENTS

CN    1632513 A  *  6/2005  ............. G01N 35/00

* cited by examiner

*Primary Examiner* — Peter J Macchiarolo
*Assistant Examiner* — Anthony W Megna Fuentes
(74) *Attorney, Agent, or Firm* — Snyder, Clark, Lesch & Chung, LLP

(57) ABSTRACT

The present disclosure relates to a system and to a method for measuring Brix of a liquid such as sap, syrup or taffy. The system for measuring Brix of a liquid comprises: a tank for receiving a volume of the liquid; a temperature reading apparatus for measuring a temperature of the liquid; a weighing apparatus for measuring a weight of the volume of liquid received in the tank; a volume measurement system for measuring the volume of the liquid received in the tank; and a computer operatively connected to the apparatuses and using the data received from the same to determine the Brix of the liquid. The method comprising providing the Brix measuring system; measuring the temperature, weight, volume of the liquid received in the tank, and determining the Brix measurement based on the data received and using the computer.

19 Claims, 3 Drawing Sheets

SYSTEM AND METHOD FOR MEASURING BRIX OF A LIQUID

CROSS REFERENCE TO RELATED APPLICATIONS

This application claims the benefit of U.S. Provisional Application No. 63/147,820 filed on Feb. 10, 2021. All documents above are incorporated herein in their entirety by reference.

TECHNICAL FIELD

The invention relates to a system and to a method for measuring Brix of a liquid.

BACKGROUND OF THE ART

The maple syrup industry, which has produced maple syrup in an artisanal way for a hundred years until the 1960s, has undergone transformation towards industrialization in order to initiate an increase in production performance and lower production costs which became prohibitive.

The classical way of harvesting sap was using buckets hanging from the trees. Thereafter, each bucket was to be emptied one by one into a large container, which was pulled by a horse, a tractor or another type of all-terrain vehicle into the sugar bush. Subsequently, the sap from the large container was sent to the sugar shack in order to be boiled using an evaporator to obtain a 66% brix sugar maple syrup. The main problem with the classical way of collecting maple sap was that maple growers were unable to expand their business due to the huge workload required to harvest sap from trees. As a result, profitability of maple syrup productions was almost impossible to reach.

In the 1970s, an alternative method of collecting maple sap has been developed. This alternative way involved collecting the sap from the maple trees using a tubing system, much the same way as in the dairy industry. This collection method was made possible thanks to spouts engaging notches of the trees and to a network of tubing and lines permanently installed on the entire sugar bush area and coupled to these spouts, where the sap of each of the maple trees is conveyed to a pumping station, which is then routed to the main sugar shack to be transformed into maple syrup. In many instances, the network of tubing is under vacuum, while in other instances the topography of the land allows the sap to descend by gravity to the pumping or harvesting station, thereby allowing the sap to be harvested in this way. Since they did not require a human presence as extensive as the classical bucket method, map sap collection systems allowed maple producers to significantly expand their businesses and make them much more profitable.

Since the 1990s, automation has become increasingly important in the production of maple syrup because finding personnel and/or operators for operating maple syrup production facilities has become a constant challenge and, the profitability of such facilities and enterprises an important factor to ensure long-term viability. Thus, in addition to relying on tubing networks to collect maple sap, producers have considered a number of technologies to improve efficiency and time required for production, including reverse osmosis apparatuses, evaporators, pumps and computerized controls for these apparatuses.

Regardless of the degree of automation of the maple syrup production in a given facility, the Brix must be monitored regularly to ensure the final product meets the 66% Brix requirement. Brix can be measured in maple sap, in the sap holding tanks, at the entry and exit of inverted osmosis and/or evaporator, and in the final product. By monitoring the Brix at these various steps of the production, the productor can monitor in real time the sugar content of the raw, intermediate and final products.

The conventional method for measuring Brix in the maple syrup industry has relied on the use of maple syrup hydrometer density meter or a hydrotherm, which is an instrument that combines the hydrometer and the thermometer into one measuring unit (the actual density of the syrup being measured can be determined directly by reading the two scales on the stem, namely a Brix scale and a density correction scale). While this type of instruments for measuring Brix is relatively inexpensive, it tends to find use in smaller scale operations and/or for punctual uses, because it requires some manipulation and cleaning by the personnel rendering it inefficient in larger scale or in automated production facilities. In some other operations, handheld digital or manual refractometers are also used, but again they tend to be used for punctual measurements, which present essentially the same drawbacks as the use of hydrometers, namely they require manipulation.

Therefore, in large scale productions, the use of inline refractometers has increased over the last years to avoid the manipulation require with more traditional Brix measurement apparatuses and measure the Brix in real time, and at various stages of maple syrup collection and production. These inline refractometers are often coupled to a controller or computer and are configured to automatically compensate or correct the Brix measurement according to the temperature of the maple sap and/or maple syrup. While they present advantages over more classical Brix measurement instruments, inline refractometers also have drawbacks. Among other things, the elevated costs of inline refractometers tend to be prohibitive for their acquisition in smaller scale operations. Further, to ensure proper and accurate Brix reading, the lens of the refractometer must be cleaned regularly, especially when it is being used with unfiltered maple sap. Another problem associated with this type of equipment is that the automatic compensation for the sap or syrup temperature for an accurate Brix reading must be adjusted regularly in order to get an optimal reading. The need for these regular adjustments are attributable to the fact that inline refractometers (e.g. Atago CM-800) are generally designed to measure the Brix of liquids having temperature that varies between 5 and 100 Celsius degrees, while the boiling temperature of high Brix sap can reach 105 degrees Celsius. Therefore, the automatic compensation of Brix measurements must be "cheated" as they are outside the maximum operational range of such inline refractometers.

There is therefore a need for a method for measuring brix of a liquid, which would overcome at least one of the above-identified drawbacks.

SUMMARY

According to a broad aspect, there is provided a system for measuring a Brix of a liquid, the system comprising:
 a tank for receiving therein a volume of the liquid;
 an inlet opening fluidly connected to the tank for conveying the liquid into the tank;
 an outlet opening fluidly connected to the tank for expelling the liquid from the tank;

a temperature reading apparatus for measuring a temperature of the liquid prior to entering the tank, while received in the tank or after being expelled from the tank;

a weighing apparatus for measuring a weight of the volume of liquid received in the tank;

a volume measurement system for measuring the volume of the liquid received in the tank a computer operatively connected to the temperature reading apparatus, the weighing apparatus and the volume measurement system and receiving data from same, the computer being programmed to determine a Brix measurement based on the data received from the temperature reading apparatus, the weighing apparatus and the volume measurement system.

In one embodiment, the computer is programmed with an algorithm correlating a Brix value of the liquid received in the tank based on the volume, the weight and the temperature of the liquid received in the tank to determine the Brix measurement of the liquid received in the tank.

In another embodiment, the temperature reading apparatus comprises at least one temperature sensor.

In still another embodiment, the at least one temperature sensor is selected from a group consisting of a thermometer, a negative temperature coefficient (NTC), thermistor, a resistance temperature detector (RTD), a semiconductor-based sensor, an infrared sensor and a bimetallic device.

In yet another embodiment, the system further comprises an inlet pipe fluidly connect to the inlet opening for conveying the liquid into the tank and an outlet pipe fluidly connected to the outlet opening for tank for expelling the liquid from the tank. In this feature, the temperature reading apparatus is mounted to at least one of the tank, the inlet pipe and the outlet pipe.

In a further embodiment, the temperature reading apparatus comprises one temperature sensor mounted to one of the tank, the inlet pipe and the outlet pipe.

In still a further embodiment, the temperature reading apparatus comprises a first temperature sensor mounted to the tank, a second temperature sensor mounted to the inlet pipe and a third temperature sensor mounted to the outlet pipe.

In yet a further embodiment, the weighing apparatus comprises at least one load cell operatively associated with the tank for measuring the weight of the volume of liquid received in the tank.

In one embodiment, the at least one load cell is supported on a floor surface, and the tank is supported onto the load cell.

In a different embodiment, the at least one load cell is suspended to a ceiling structure and the tank is suspended by the load cell.

In another embodiment, the tank has a defined maximum volume, and the volume measurement system is configured for filling the tank with the liquid to the defined maximum volume.

In yet another embodiment, the volume measurement system further comprises gas removing means associated with the tank for removing gas present in the liquid contained in the tank.

In an additional embodiment, the volume measurement system comprises at least one level sensor operatively associated with the tank, the computer being configured for receiving data from the level sensor and extrapolating a volume of liquid contained in the tank for predetermined levels.

In another embodiment, the system further comprises a Brix reading apparatus for measuring the Brix of the liquid prior to entering the tank, while received in the tank or after being expelled from the tank, the computer being operatively connected to the Brix reading apparatus and receiving data from same, the computer being programmed to account for the data received from the Brix reading apparatus to determine the Brix measurement.

In still another embodiment, the Brix reading apparatus comprises a refractometer.

In yet another embodiment, the liquid is selected from a group consisting of sap, syrup and taffy. Preferably, the sap comprises maple sap and the syrup comprises maple syrup.

According to another broad aspect, there is provided a method for measuring Brix from a liquid, the method comprising:

Providing a system as described above;

Measuring the temperature of the liquid received in the tank using the temperature reading apparatus;

Measuring the weight of the liquid received in the tank using the weighing apparatus;

Measuring the volume of the liquid received in the tank using the volume measurement system;

Receiving data from the temperature reading apparatus, the weighing apparatus and the volume measurement system; and Determining the Brix measurement based on the data received from the temperature reading apparatus, the weighing apparatus and the volume measurement system using the computer.

BRIEF DESCRIPTION OF THE DRAWINGS

Having thus generally described the nature of the invention, reference will now be made to the accompanying drawings, showing by way of illustration example embodiments thereof and in which.

DETAILED DESCRIPTION OF EMBODIMENTS

Figure 1:
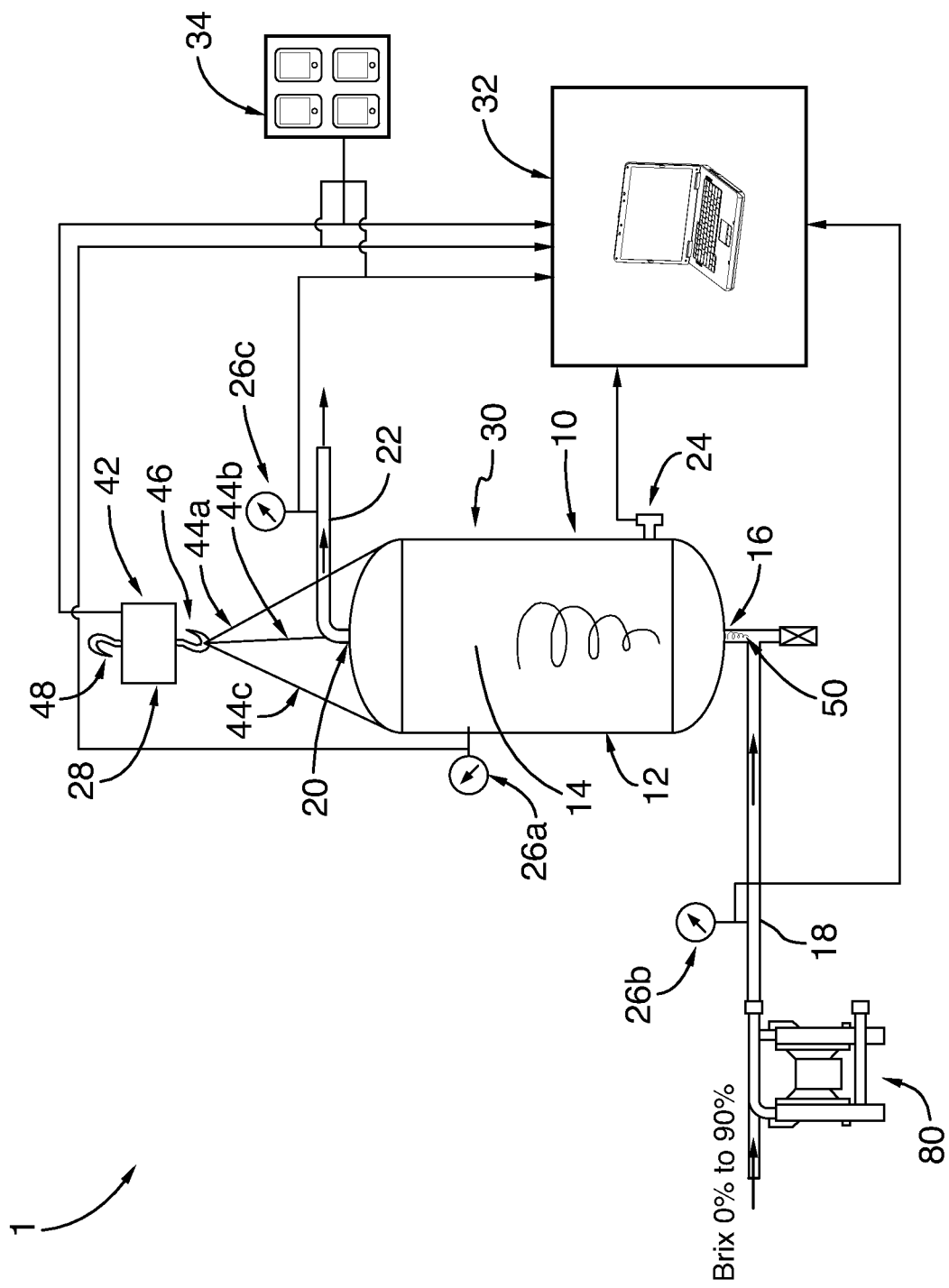
FIG. 1 is a schematic diagram of a system for measuring a Brix of a liquid in accordance with one embodiment.

In the following description, the same numerical references refer to similar elements. Furthermore, for the sake of simplicity and clarity, namely so as to not unduly burden the figures with several reference numbers, not all figures contain references to all the components and features, and references to some components and features may be found in only one figure, and components and features of the present disclosure which are illustrated in other figures can be easily inferred therefrom. The embodiments, geometrical configurations, materials mentioned and/or dimensions shown in the figures are optional and are given for exemplification purposes only.

Moreover, it will be appreciated that positional descriptions such as "above", "below", "forward", "rearward", "left", "right" and the like should, unless otherwise indicated, be taken in the context of the figures only and should not be considered limiting. The use of "including," "comprising," or "having" and variations thereof herein is meant to encompass the items listed thereafter and equivalents thereof as well as additional suitable items. Unless specified or limited otherwise, the terms "mounted," "connected," "supported," and "coupled" and variations thereof are used broadly and encompass both direct and indirect mountings, connections, supports, and couplings and are thus intended to include direct connections between two members without any other members interposed therebetween and indirect connections between members in which one or more other members are interposed therebetween. Further, "connected" and "coupled" are not restricted to physical or mechanical connections or couplings. Additionally, the words "lower", "upper", "upward", "down" and "downward" designate directions in the drawings to which reference is made.

It is to be understood that the phraseology and terminology employed herein is not to be construed as limiting and are for descriptive purpose only. The principles and uses of the teachings of the present disclosure may be better understood with reference to the accompanying description, figures and examples. It is to be understood that the details set forth herein do not construe a limitation to an application of the disclosure.

Furthermore, it is to be understood that where the claims or specification refer to "a" or "an" element, such reference is not be construed that there is only one of that element. It is to be understood that where the specification states that a component, feature, structure, or characteristic "may", "might", "can" or "could" be included, that particular component, feature, structure, or characteristic is not required to be included.

Variants, examples and preferred embodiments of the invention are described hereinbelow. According to one embodiment, there is provided a system and a method for measuring, in continuous (real time) or not, the Brix of a liquid, and especially the Brix of maple sap or maple syrup, that are relatively inexpensive, that avoid the need of frequent reading of lenses of inline refractometers and that compensate or correct the Brix for temperatures ranging between 5 Celsius degrees and 110 Celsius degrees. In this embodiment, the system and method can measure Brix of 0% to 90%.

According to this embodiment, and referring to FIG. 1, the system 1 comprises a reservoir or tank 10 having a peripheral wall 12 defining a chamber 14 for receiving a liquid therein, an inlet opening 16 fluidly coupled to an inlet pipe 18, for conveying the liquid into the chamber 14 of the reservoir 10, an outlet end 20 operatively coupled to an outlet pipe 22, for evacuating the liquid from the chamber 14 of the reservoir 10.

The system 1 further comprises a plurality of temperature sensors 26a to 26c for measuring or evaluating the temperature of the liquid contained in chamber 14, inlet pipe 18, or outlet pipe 22, a weighing system 28 for measuring the weight of the liquid contained in the tank 10 and a volume measurement system 30 for measuring or determining the volume of the liquid contained in the tank 10. The system 1 also comprises a controller or computer 32 in communications with the at least one temperature sensor 26, the weighing system 28 and the volume measurement system 30 and receiving inputs or data from them, the computer 32 being programmed to process the inputs or data received from the at least one temperature sensor 26, the weighing system 28 and the volume measurement system 30 determined a Brix measurement of the liquid contained in the tank 10, as it will be described in greater details below.

As it will be apparent, the controller or computer 32 may be a programmable logic controller (PLC) or programmable controller or a supervisory control and data acquisition (SCADA) system.

As it will be appreciated, the system 1 could be used in connection with a number of tanks (better seen in FIG. 3) for holding either sap, syrup or taffy, where tank 10 could be a container storage tank, a stainless steel tank, a plastic tank, an isolated syrup calibration tank, a vertical silos, or any other type of tank, whether horizontal or vertical, and regardless of the material(s) from which such tank is manufactured. Likewise, it will be appreciated that tank 10 could be used at various steps of maple syrup productions, whether in the pumping station in the sugar bush where it receives maple sap from the tubing collecting the sap from maple trees, in a storage station closer to the sugar shack, prior of after reverse osmosis, prior to boiling, between the various boiling stages and/or after the boiling process but before filling barrels. As such, the inlet and/or outlet pipes 18, 22 can also be made of different materials, depending on the stage of maple syrup production the tank 10, inlet or outlet pipes 18, 22 are being used.

In the embodiment illustrated in FIG. 1, the system 1 comprises three temperature sensors 26a-26c that are used to provide the computer with a measure or indication of the temperature of the liquid contained in the chamber of the thank 10, so as to account for such temperature in the calculation of the Brix of the liquid. In this embodiment, temperature sensors 26a-26c are positioned in various locations to provide a more accurate reading or indication of the liquid temperature. More specifically, the system comprises a temperature sensor 26a mounted to the peripheral wall 12 of the tank 10, a temperature sensor 26b mounted to the inlet pipe 18 and a temperature sensor 26c mounted the outlet pipe 22.

As it will be best described below, in other embodiments, the system 1 could be provided with a different number of sensors and/or temperature sensors at other locations. For instance, the system 1 could be provided with two temperature sensors, mounted to the inlet and outlet pipes 18, 22 (but no sensor mounted to the tank 10) or to the tank 10 and to one of the inlet pipe 18 and the outlet pipe 22. Alternatively, the system 1 could be provided with only one sensor, mounted either to the inlet pipe 18, to the outlet pipe 22 or to the tank 10. In this embodiment, the temperature sensors 26a-26c are simultaneously connected to the computer 32 to provide a compensation of the Brix based on aggregated temperature data from these three locations.

As it will be appreciated, various types of temperature sensors could be used to measure the temperature of the liquid in the inlet pipe 18 the chamber 14 of the tank 10 and/or in the outlet pipe 22, including thermometers, negative temperature coefficient (NTC), thermistors, resistance temperature detectors (RTDs), semiconductor-based sensors, infrared sensors, bimetallic devices and the like. In one embodiment, a single temperature sensor is used to measure or extrapolate the temperature of the liquid in the reservoir.

To provide the computer 32 with the weight of the liquid contained in the tank 10, the weighing system 28 is provided. In the embodiment illustrated in FIG. 1, the weighing system 28 is configured such that the tank 10 is supported by or hang to a weight sensing sensor 42 comprising a upper hook 48 and a lower hook 46, for instance a tension load cell (e.g. a tension weight module). In such an embodiment, the tank 10 is provided with a plurality of suspension cables 44a-44d (only suspension cables 44a to 44c are shown in FIG. 1), or alternatively to frame members (not shown). The suspension cables 44a to 44d are configured to allow the tank 10 to be hang to the lower hook 46 of the weight sensor 42, which attaches to or suspends from a structure such a ceiling beam, a truss or any other type of structure (not shown) using the upper hook 48.

As is will be apparent, the weight sensor 42 and/or computer 32 can be configured to tare weight of the empty tank 10 and of the various components of the system that can be attached thereto (e.g. the pipes 18, 22 and the like) and/or the inertial frame of reference of the system so that the weight of the liquid contained in the tank 10 is measured with precision and excludes any weight measurements not attributable to the liquid contained in the tank 10.

Further, weight sensor 42 and/or computer 32 can be configured to account for other factors that could affect the measurement of the weight, for instance the way the tank is supported by the weight sensor, the tension forces in the suspension cables 44a to 44c, the length of the suspension cables 44a to 44c, and any other forces due to movement of the tank 10 and of the various components of the system that can be attached thereto (e.g. the pipes 18, 22 and the like), changes due to the temperature of the liquid contained in the chamber 14 and or the external temperature, as well as, coefficients of thermal changes of the different materials used, which tend to expand under warm temperatures and to contract under colder temperatures.

To correlate the weight of the liquid contained in the tank 10 with its volume, the volume measurement system 30 is provided. The embodiment illustrated in FIG. 1, the volume measurement system 30 comprises the tank 10, for which the precise volume is known at a standard temperature (e.g. 20 Celsius degrees), as well as a whirlpool or venturi device 50 for evacuating air bubbles that may be present in the liquid, and which may affect the actual volume of the liquid contained in the in thank 10. By ensuring that the tank 10 is completely filled with liquid (e.g. maple sap, maple syrup or taffy) and that all air, bubbles or gasses contained the liquid are evacuated using the whirlpool device 50 or any other similar device that would allow for such evacuation, the exact volume of liquid for which the weight is measured is known with precision, and the volume information or data can be sent to or factored in by the computer or controller 32, to account for this information in the calculation or determination of the Brix measurement.

As it will be appreciated, the volume of the tank 10 may itself be affected by the temperature of the liquid contained in the chamber 14 and or the external temperature, as materials tend to expand under warm temperatures and to contract under colder temperatures. As it will further be appreciated, this variation of volume of the tank 10 would in turn affect the exact volume of liquid contained in the tank 10 and measured at a given level. As such, the volume of the tanks may be determined or calibrated at a standard temperature (e.g. the volume at 20 Celsius degrees), and a correction based on the temperature internal and/or external to the tank 10 can be applied to correct the volume of the tank 10 according to the temperature (and thus to the volume of liquid contained therein). Like the three temperature sensors 26a-26c for measuring the temperature of the liquid contained in the chamber 14, various types of temperature sensors could be used to determine the temperature external to the tank 10, thereby provide a correction value for the volume of the tank 10.

In an alternate embodiment, the system 1 could also comprise an optional Brix measurement apparatus such as an inline refractometer 24 operatively coupled to the chamber 14, the inlet pipe 18 or the outlet pipe 22 for directly measuring the Brix of the liquid contained in the chamber 14 of the tank 10 or for directly measuring the Brix of the liquid circulating in the inlet and/or outlet pipes 18, 22. In such an alternate embodiment, the optional inline refractometer 24 is in communication with the computer or controller 32, much like the three temperature sensors 26a-26c, the weighing system 28 and the volume measurement system 30. As such, the computer 32 receives inputs or data from the optional refractometer 24, in addition to receiving data or inputs from the temperature sensors 26a-26c, the weighing system 28 and the volume measurement system 30. In this embodiment, the computer or controller 32 may be programmed to process the inputs or data received from the at least one of temperature sensor 26a-26c, the weighing system 28 and the volume measurement system 30, and the refractometer 24 either to apply a correction to the Brix measurement based on the weight (mass) of the liquid contained in the tank 10, its volume and temperature as described above, as well as, to apply a correction to the Brix readings from the inline refractometer 24, or to provide a comingled Brix measurement value based on the Brix measurement based on the weight (mass) of the liquid contained in the tank 10, its volume and temperature as described above, and the readings from the refractometer 24.

As it will be appreciated, various types of inline refractometers 24 could be used. Further, the inline refractometer could be mounted to the piping system (e.g. the inlet pipe 18 or the outlet pipe 22), inside the chamber 14 on the peripheral wall 12 of the tank 10, or otherwise mounted in the chamber 14. While in the above embodiment, the system 1 has been described in connection with a single optional refractometer 24, it will be appreciated that the system could comprise multiple refractometers (e.g. similar to refractometer 24).

In operation, the system 1 comprises the inlet pipe 18 which may be in fluid connection with a network of pipes (not shown), said network of pipes may be connected to a number of trees (not shown) for collecting the sap therefrom. In one embodiment, the inlet pipe 18 may be connected to a number of maple trees (not shown) and the system 1 is configured for measuring Brix from maple sap, taffy and/or maple syrup.

In embodiments it will be understood that the inlet pipe 18 could instead be connected to a different type of trees, and the system 1 be configured to measure the Brix of a different type of sap or liquid. In some embodiment, the network of pipes is linked to intervening devices such as pumps (see, for instance, pump 80 in FIG. 1), to facilitate the transport of sap from the trees (not shown) to the inlet pipe 18.

While the sap in conveyed in the inlet pipe 18, it temperature is measured for a first time, when the system 1 is equipped with a temperature sensor in the inlet pipe 18 (e.g. temperature sensor 26b shown in FIG. 1), and the temperature data is sent to the computer or controller 32, either through a wired connection or a wireless connection, to be processed by the computer. The sap or liquid then goes through the inlet opening 16, to reach the chamber 14 of the tank 10, until a volume of sap or liquid to be measured is contained in the tank 10.

While in operation, the temperature of the liquid contained in the tank 10 is measured with the temperature sensor mounted to the tank (e.g. temperature sensor 26a in FIG. 1), and the temperature data is sent to the computer or controller 32, either through a wired connection or a wireless connection, to be processed. At that point, the weight of the liquid contained in the tank 10 is measured by the weighing system 28 and the volume of the liquid is determined by the volume measurement system 30. The data obtained by the weighing system 28 and the volume measurement system 30 is sent to the computer or controller 32 by wired or wireless connection, also to be processed. At that point, when in embodiments the system 1 is provided with an optional refractometer 24, the refractometer 24 takes measurement of the Brix of the liquid contained in the tank 10, and also sends the measurement to the computer or controller 32, again by wired connection or wireless connection.

Still referring to FIG. 1, in embodiments, When the liquid is allowed to exit the chamber 14 of the tank 10, for instance by opening a valve (not shown), the liquid exits the chamber 14 through the outlet opening 20 to flow through the outlet pipe 22. When the system 1 is equipped with a temperature sensor in the outlet pipe 22 (e.g. temperature sensor 26c in FIG. 1), the temperature sensor measures the temperature of the liquid in the outlet pipe 22 and sends data to the computer, to be processed.

In embodiments, upon receipt of the temperature data from the temperature sensors 26a, 26b and/or 26c, the weight of the liquid from the weighing system 28 and the volume of the liquid from the volume measurement system 30 (and, when applicable, Brix data from the optional refractometer 24), the computer or controller 32 applies a preprogram algorithm accounting for the temperature of the liquid, its weight and volume to apply to determine a Brix measurement (or to apply an appropriate correction or comingled Brix measurement value by also using the data measurement from the optional refractometer). For instance, in one embodiment, the computer 32 is programmed with an algorithm correlating a Brix value of the liquid received in the tank 10 based on the volume, the weight and the temperature of the liquid received in the tank, in order to determine the Brix measurement of the liquid received in the tank 10. As it will be appreciated, such algorithm may take multiple forms, and can include preset tables correlating Brix measurement values to weight (mass), volume and temperature of the liquid (e.g. maple sap syrup, or taffy), or mathematical formulas for dynamically calculating the Brix based on weight, volume and temperature of the liquid contained in the tank 10 or elsewhere in the system 1. As it will be appreciated, the system may also use data from the optional refractometer 24 to more accurately determine the Brix measurement and/or make the necessary corrections.

To facilitate the operation of the computer or controller 32 and of the system 1, and the adjustment of the various parameters, the computer can be provided with a graphical interface 34. Such interface allow the control and monitoring of the various elements of the system (e.g. the temperature sensors 26, the level sensor 50, the weighing system, etc.), and can be access directly from the computer 32 or remotely using internet or other type of connection, whether wired or wireless, using other computers or personal handheld electronic devices such a smart phones or tablets. Such interface 34 may be an input interface.

As it will be appreciated, it may be desirable to use to system 1 to determine the Brix value of different types of liquids. For instance, the system 1 may be used to measure the Brix of maple syrup, and then of maple sap, taffy or a different type of liquid. In such circumstances, the system 1 may be cleaned between the various Brix measurements, simply by circulating water and/or a cleaning agent in the inlet pipe 18, tank 10, outlet pipe 20 and any other relevant part of the system 1.

Figure 2:
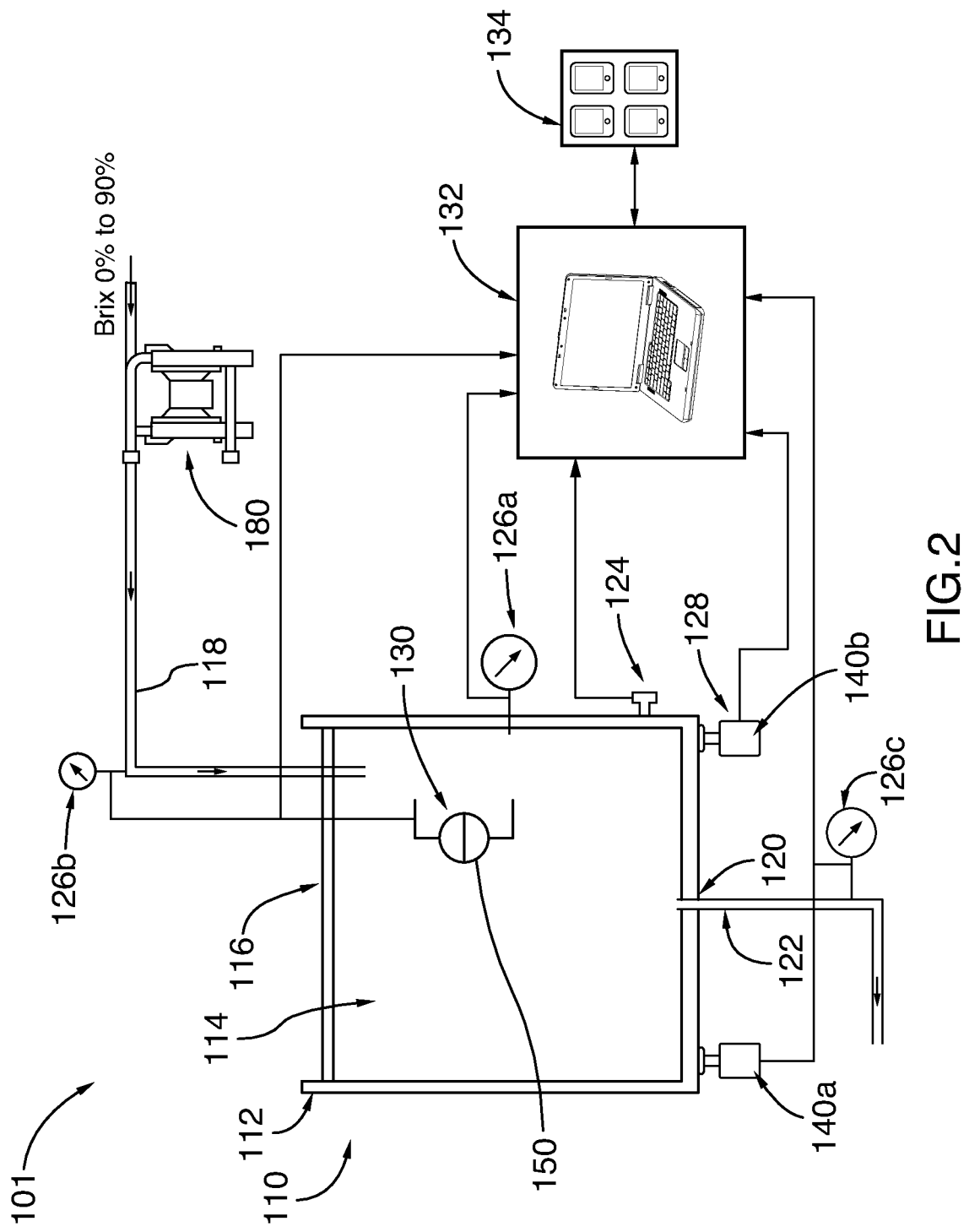
FIG. 2 is a schematic diagram of a system for measuring a Brix of a liquid in accordance with another embodiment.

Turning now to FIG. 2, there will be described an alternative embodiment of a system 101 for measuring, in continuous (real time) or not, the Brix of a liquid. According to this embodiment, the system 101 comprises a reservoir or tank 110 having a peripheral wall 112 defining a chamber 114 for receiving a liquid therein, a top opening 116 in alignment with an inlet pipe 118, for conveying the liquid into the chamber 114 of the tank 110, an outlet end 120 defined at the bottom of the tank 110 and operatively coupled to an outlet pipe 122, for evacuating the liquid from the chamber 114 of the reservoir 110.

The system 101 further comprises a temperature sensor 126a for measuring or evaluating the temperature of the liquid contained in chamber 114, a weighing system 128 for measuring the weight of the liquid contained in the tank 10 and a volume measurement system 130 for measuring or determining the volume of the liquid contained in the tank 110. The system 101 also comprises a controller or computer 132 in communications with the temperature sensor 126a, the weighing system 128 and the volume measurement system 130 and receiving inputs or data from them, the computer 132 being programmed to process the inputs or data received from the temperature sensor 126a, the weighing system 128 and the volume measurement system 130 determined a Brix measurement of the liquid contained in the tank 110, as it will be described in greater details below.

As it will be apparent, the controller or computer 132 may be a programmable logic controller (PLC) or programmable controller or a supervisory control and data acquisition (SCADA) system.

Much like the system 1, the system 101 could be used in connection with a number of tanks for holding either sap or syrup, where tank 110 could be a container storage tank, a stainless steel tank, a plastic tank, an isolated syrup calibration tank, a vertical silos, or any other type of tank, whether horizontal or vertical, and regardless of the material(s) from which such tank is manufactured. Likewise, it will be appreciated that tank 110 could be used at various steps of maple syrup productions, whether in the pumping station in the sugar bush where it receives maple sap from the tubing collecting the sap from maple trees, in a storage station closer to the sugar shack, prior of after reverse osmosis, prior to boiling, between the various boiling stages and/or after the boiling process but before filling barrels. As such, the inlet and/or outlet pipes (118, 122) can also be made of different materials, depending on the stage of maple syrup production the tank 110, inlet 118 or outlet pipes 122 are being used. The inlet and/or outlet pipes (118, 122) may be completely made of flexible material or partially made of flexible material. Flexible pipes may include steel, ductile iron, thermoplastics such as Polyvinyl Chloride (PVC) and High Density Polyethylene (HDPE), thermosetting plastics such as fiberglass-reinforced polymer (FRP), bar-wrapped concrete cylinder pipe, and corrugated steel pipes.

The sensor 126a is used to provide the computer or controller 132 with a measure of the temperature of the liquid contained in the chamber of the thank 110, so as to account for such temperature in the calculation of the Brix of the liquid. In one embodiment, the temperature sensor 126a is operatively mounted to the tank 110 to measure the temperature of the liquid contained therein.

In an alternate embodiment, the system 101, like system 1, could include a plurality of temperature sensors mounted at different locations in the system 101, for instance three temperature sensors including one sensor in the inlet pipe 126b, one sensor in the chamber of the tank 110 and/or one sensor in the outlet pipe 126c, to provide a compensation of the Brix based on aggregated temperature data from these three locations.

In other embodiments, the system 101 could be provided with a different number of sensors and/or temperature sensors at other locations. For instance, the system 101 could be provided with two temperature sensors, mounted to the inlet and outlet pipes (126b, 126c) but no sensor mounted to the tank 110. Alternatively, the system 101 could be provided with only one sensor, mounted either to the inlet pipe 126b or to the outlet pipe 126c.

As it will be appreciated, various types of temperature sensors could be used to measure the temperature of the liquid in the chamber 114 of the tank 110, including thermometers, negative temperature coefficient (NTC), thermistors, resistance temperature detectors (RTDs), semiconductor-based sensors, infrared sensors, bimetallic devices and the like.

To provide the computer or controller 132 with the weight of the liquid contained in the tank 110, the weighing system 128 is provided. In the illustrated embodiment, the weighing system 128 comprises a plurality of weight sensors such as load cells, onto which the tank 110 is supported. Such weight sensors could include, for instance, compression load cells, compression load modules, strain gauge load cells, single point load cells or any other type of electronic or digital weight sensors. Such weight sensors could include, for instance, compression load cells, compression load modules, strain gauge load cells, single point load cells or any other type of electronic or digital weight sensors. For instance, where a tank 110 having a square or rectangular base is used (as shown in FIG. 2), the tank 110 can rest on 4 compression load cells 140a-140d (only load cells 140a-140d being shown in FIG. 2), each load cells 140a-140d being positioned at one corner of the square or rectangular-shaped tank 110. In such an embodiment, the load or weight sensed by each load cell 140a-140d is sent and treated by the controller or computer 132, to determine the weight of the liquid contained in the tank 110 and to account for such weight in the calculation or determination of the Brix measurement.

As is will be apparent, the load cells 140a-140d and/or computer or controller 132 can be configured to tare weight of the empty tanks 110 and of the various components that can be attached thereto (e.g. pipes and the like) so that the weight of the liquid contained in the tank 110 is measured with precision and excludes any weight measurements not attributable to the liquid in the tank 110.

Further, in embodiments, the load cells 140a-140d and/or computer or controller 132 can be configured to account for other factors that could affect the measurement of the weight, for instance the position of the various load cells relative to the floor or ground surface, as well as any irregularities on the floor or ground surface that could affect the measurements taken by the load cells. As it will be appreciated, the number and position of load cells can vary greatly depending on the configuration and shape of the reservoir or tank, the space and nature of the surface on which these load cells rests and other factors. Thus, in some embodiment, the tank 110 could be supported on, or suspended to a single load cell or weight sensor, while in other embodiments a plurality of load cells or weight sensors may be desirable.

To correlate the weight of the liquid contained in the tank 110 with its volume, the volume measurement system 130 is provided. In one embodiment, the volume measurement system 130 comprises the tank 110, for which the volume at various predetermined levels is known, as well as at least one level sensor 150 for measuring the level of liquid in the tanks 110. By determining the level of the liquid contained in the tank 110, and knowing the volume of the tank 110 at the various predetermined levels (either as preset values or by calculation), it becomes possible to extrapolate the volume of liquid contained in the tank 110, and to send the relevant information or data to the computer or controller 132, to account for this information in the calculation or determination of the Brix measurement.

As it will be appreciated, the volume of the tank 110 may itself be affected by the temperature of the liquid contained in the chamber 114 and or the external temperature, or the materials used in making the tank, as materials tend to expand under warm temperatures and to contract under colder temperatures. As it will further be appreciated, this variation of volume of the tank 110 would in turn affect the exact volume of liquid contained in the tank 110 and measured at a given level. As such, the volume of the tanks may be determined or calibrated at a standard temperature (e.g. the volume at 20 Celsius degrees), and a correction based on the temperature internal and/or external to the tank 110 can be applied to correct the volume of the tank 110 according to the temperature (and thus to the volume of liquid contained therein). Like the temperature sensor 126 for measuring the temperature of the liquid contained in the chamber 114, various types of temperature sensors could be used to determine the temperature external to the tank 110, to provide a correction value for the volume of the tank.

In one embodiment, the level sensor 150 is mounted to peripheral wall 112 of the tank 110, either directly or via an intervening structure such as a bracket, to extend in the internal chamber 114 of the tank 110 and to measure the level of liquid contained therein. The level sensor 150 could be of any type suitable for such an application, including of level sensor such as optical level switches, capacitance level sensors, ultrasonic sensors, microware sensors, radar sensors, vibrating sensors, turning fork sensors, conductive sensors, resistance sensors, float switches and the like.

In an alternate embodiment, the system 101 could also comprises a Brix measurement apparatus such as an inline refractometer 124 operatively coupled to the chamber 114, the inlet pipe 118 or the outlet pipe 122 for directly measuring the Brix of the liquid contained in the chamber 114 of the tank 110 or circulating in the inlet and/or outlet pipes (118, 122).

In this embodiment, the inline refractometer 124 is in communication with the computer 132, much like the temperature sensors 126a, 126b, 126c, the weighing system 128 and the volume measurement system 130. As such, the computer 132 receives inputs or data from the refractometer 124, in addition to receiving data or inputs from the temperature sensors 126a, 126b, 126c, the weighing system 128 and the volume measurement system 130. In this embodiment, the computer or controller 132 is programmed to process the inputs or data received from the temperature sensors 126a, 126b, 126c, the weighing system 128 and the volume measurement system 130 and the refractometer 124 either to apply a correction to the Brix measurement based on the weight (mass) of the liquid contained in the tank 110, its volume and temperature as described above, to apply a correction to the Brix readings from the inline refractometer 124, or to provide a comingled Brix measurement value otherwise based on the Brix measurement based on the weight (mass) of the liquid contained in the tank 110, its volume and temperature as described above and the readings from the refractometer 124.

As it will be appreciated, various types of inline refractometers 124 could be used. Further, the inline refractometer 124 can be mounted to the piping system (e.g. the inlet pipe 118 or the outlet pipe 122, inside the chamber 114 on the peripheral wall 112 of the tank 110, or otherwise mounted in the chamber 114.

In one embodiment, the refractometer 124 is operatively coupled to a cleaning system (not shown) allowing a cleaning liquid to circulate and recirculated to clean the lens of the refractometer 124. While in the above embodiment, the system 101 has been described in connection with a single optional refractometer 124, it will be appreciated that the system could comprise multiple optional refractometers (not shown) (e.g. similar to refractometer 124).

In operation, the system 101 comprises the inlet pipe 118 which may be fluid connection with a network of pipes (not shown) connected to a number of trees (not shown) for collecting the sap therefrom. In one embodiment, the outlet pipe 122 is connected to a number of maple trees (not shown) and the system 101 is configured for measuring Brix from maple sap, taffy and/or maple syrup, but it will be understood that the inlet pipe 118 could instead be connected to a different type of trees and the system 101 be configured to measure the Brix of a different type of sap, taffy or liquid. In some embodiment, the network of pipes (not show) may be linked to intervening devices such as pumps 180, to facilitate the transport of sap from the trees to the inlet pipe 118.

While the sap or liquid is conveyed in the inlet pipe, its temperature can be measured for a first time, when the system 101 is equipped with a temperature sensor in the inlet pipe 118, and the temperature data is sent to the computer or controller 132, either through a wired connection or a wireless connection, to be processed by the computer or controller 132. The sap, taffy, or liquid then goes through the top opening 116, to reach the chamber 114 of the tank 110, until a volume of sap, taffy or liquid is contained in the tank 110.

While in operation, the temperature of the liquid contained in the tank 110 is measured with the temperature sensor 126a mounted to the tank 110, and the temperature data is sent to the computer or controller 132, either through a wired connection or a wireless connection, to be processed. At that point, the weight of the liquid contained in the tank 110 is measured by the weighing system 128 and the volume of the liquid is determined by the volume measurement system 130. The data obtained by the weighing system 128 and the volume measurement system 130 is sent to the computer or controller 132 by wired or wireless connection, also to be processed. At that point, when the system 101 is provided with an optional refractometer 124, the refractometer 124 takes measurement of the Brix of the liquid contained in the tank 110 or at different points (e.g. inlet pipe 118 or the outlet pipe 122), and also sends the measurement to the computer or controller 132, again by wired connection or wireless connection.

When the liquid is allowed to exit the chamber 114 of the tank 110, for instance by opening a valve (not shown), the liquid exits the chamber 114 through the outlet opening 120 to flow through the outlet pipe 122. When the system 101 is equipped with a temperature sensor 126c in the outlet pipe 122, the temperature sensor measures the temperature of the liquid in the outlet pipe and sends data to the computer or controller 132, to be processed.

Upon receipt of the temperature data from the temperature sensors 126a, 126b or 126c, the weight of the liquid from the weighing system 128 and the volume of the liquid from the volume measurement system 130 (and, when applicable, Brix data from the optional refractometer 124), the computer or controller 132 applies a preprogram algorithm accounting for the temperature of the liquid, its weight and volume to determine a Brix measurement (or to apply an appropriate correction or comingled Brix measurement value). For instance, in one embodiment, the computer or controller 132 is programmed with an algorithm correlating a Brix value of the liquid received in the tank 110 based on the volume, the weight and the temperature of the liquid received in the tank 110, in order to determine the Brix measurement of the liquid received in the tank 110. As it will be appreciated, such algorithm may take multiple forms, and can include preset tables correlating Brix measurement values to weight (mass), volume and temperature of the liquid (e.g. maple sap or syrup), or mathematical formulas for dynamically calculating the Brix based on weight, volume and temperature of the liquid contained in the tank 110, data from the optional refractometer 124, or elsewhere in the system 101.

To facilitate the operation of the computer or controller 132 and of the system 101, and the adjustment of the various parameters, the computer or controller can be provided with a graphical interface 134. Such interface allow the control and monitoring of the various elements of the system (e.g. the temperature sensors (126a, 126b, 126c), the level sensor 150, the weighing system 128, etc.), and can be accessed directly from the computer or controller 132, or remotely using internet or other type of connection, whether wired or wireless, using other computers or personal handheld electronic devices such a smart phones or tablets. Such interface 134 may be an input interface.

As it will be appreciated, it may be desirable to use to system 101 to determine the Brix value of different types of liquids. For instance, the system 101 may be used to measure the Brix of maple syrup, and then of maple sap, taffy or a different type of liquid. In such circumstances, the system 101 may be cleaned between the various Brix measurements, simply by circulating water and/or a cleaning agent in the inlet pipe 118, tank 110, outlet pipe 120 and any other relevant part of the system 101.

Figure 3:
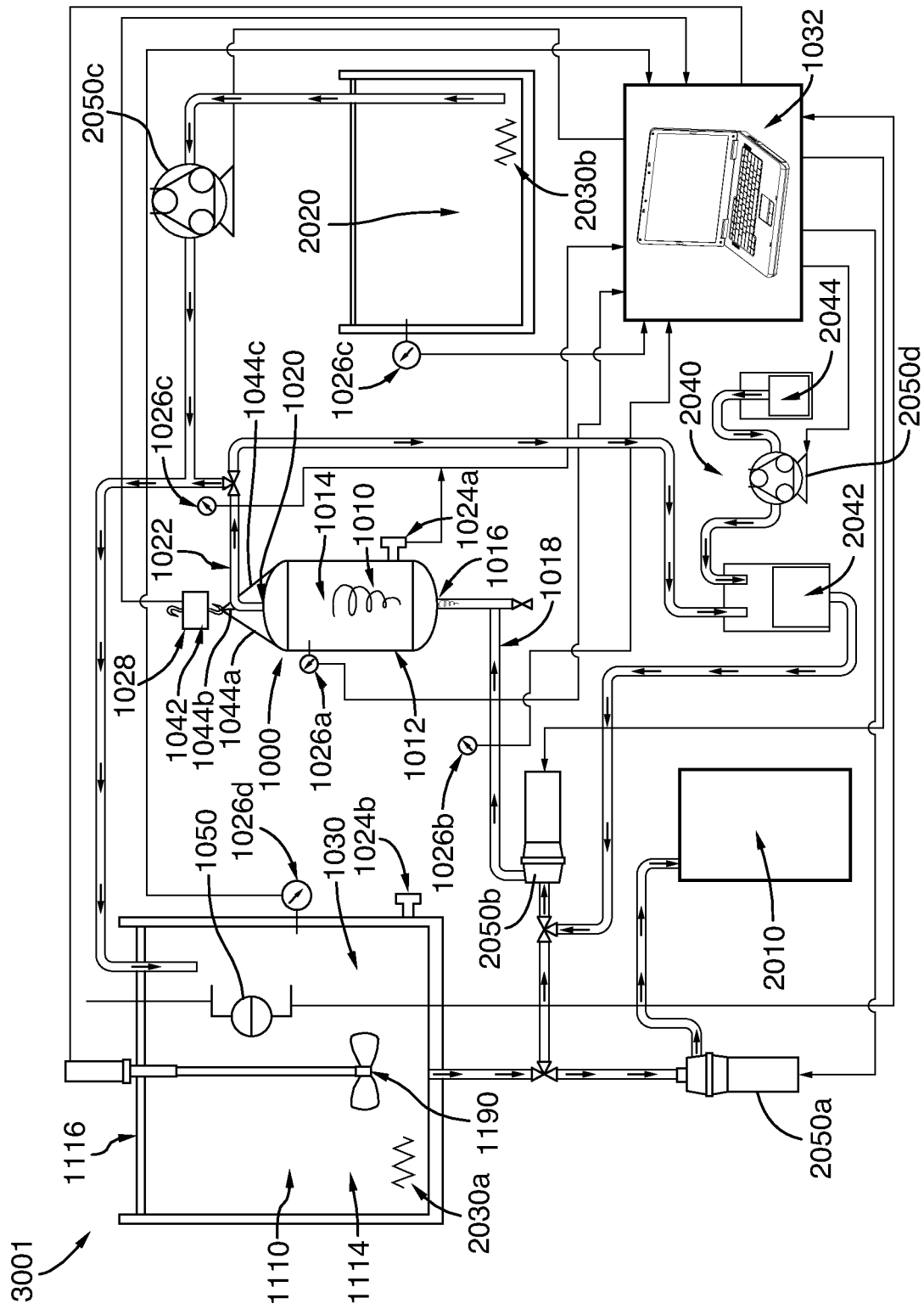
FIG. 3 is a schematic diagram of a system allowing the calibration of a system for measuring Brix similar to the one shown in FIG. 1.

Referring now to FIG. 3, in embodiments, there is provided of a method and system for measuring the Brix of maple sap in continuous (real time) or not 3001, wherein said method allows for the automatic calibration of the Brix by using a volume measurement and density calibration system 1030, said method integrating the a system 1000 for measuring the Brix of maple sap in continuous (real time) or not. As provided, the method for measuring Brix from a liquid comprises: providing the system 1000 comprising a tank 1010 for receiving therein a volume of the liquid, an inlet opening 1020 fluidly connected to the tank 1010 for conveying the liquid into the tank 1010; an outlet opening 1016 fluidly connected to the tank for expelling the liquid from the tank; a temperature reading apparatus (1026a, 1026b, 1026c) for measuring a temperature of the liquid prior to entering the tank 1010, while received in the tank or after being expelled from the tank; a weighing apparatus 1028 for measuring a weight of the volume of liquid received in the tank; volume measurement and density calibration system 1030 for measuring the volume of the liquid received in the tank and calibrating the Brix; a computer or controller 1032 operatively connected to the temperature reading apparatus (1026a, 1026b, 1026c), the weighing apparatus 1028 and the volume measurement and density calibration system 1030 and receiving data from same, the computer or controller 1032 being programmed to determine a Brix measurement based on the data received from the temperature reading apparatus (1026a, 1026b, 1026c), the weighing apparatus 1028 and volume measurement and density calibration system 1030 and receiving data from same; measuring the temperature of the liquid received in the tank 1010 using the temperature reading apparatus (1026a, 1026b, 1026c); measuring the weight of the liquid received in the tank 1010 using the weighing apparatus 1028; measuring the volume and density of the liquid received in the tank 1010 using the volume measurement and density calibration system 1030; receiving data from the temperature reading apparatus (1026a, 1026b, 1026c), the weighing apparatus 1028 and volume measurement and density calibration system 1030; and using the computer to determine the Brix measurement based on the data received from the temperature reading apparatus (1026a, 1026b, 1026c), the weighing apparatus 1028 and the volume measurement and density calibration system 1030. The computer or controller 1032 optionally being programmable for calibrating the Brix measurements thanks for the data received from the volume measurement and density calibration system 1030.

As it will be apparent, the controller or computer 1032 may be a programmable logic controller (PLC) or programmable controller, or a supervisory control and data acquisition (SCADA) system.

Still referring to FIG. 3, it will be appreciated the reservoir or tank 1010 comprises a peripheral wall 1012 defining a chamber 1014 for receiving a liquid therein, an inlet opening 1016 fluidly coupled to an inlet pipe 1018, for conveying the liquid into the chamber 1014 of the reservoir 1010, an outlet end 1020 operatively coupled to an outlet pipe 1022, for evacuating the liquid from the chamber 1014 of the reservoir 1010.

As it will be appreciated, the weighing system 1028 may be configured such that the tank 1010 is supported by or hang to a weight sensing sensor 1042, for instance a tension load cell (e.g. a tension weight module). In such an embodiment, the tank 1010 is provided with a plurality of suspension cables 1044a to 1044d (only suspension cables 1044a to 1044c being shown in FIG. 3), or alternatively to frame members (not shown), allowing to tank 1010 to be hang to a lower hook of the weight sensor 1042, which weight sensor 1042 also comprises an upper hook for attaching or suspending the weight sensor 1042 to a structure such a ceiling beam (not shown), a truss or any other type of structure (not shown) to which the tank 1010 can be suspended.

As it is further appreciated in FIG. 3, the Brix measurement apparatus may also comprise an inline refractometer 1024a operatively coupled to the chamber 1014.

Still referring to FIG. 3, in embodiments, it will be appreciated that an optional volume measurement and density calibration system 1030 may be fluidly coupled with the reservoir or tank 1010, wherein the outlet pipe 1022 directs the liquid received in the tank 1010 towards the volume measurement and density calibration system 1030.

In embodiments, the volume measurement and density calibration system 1030 may comprise a top opening 1116, to reach the chamber 1114 of the tank 1110, until a volume of sap is contained in the tank 1110. The volume measurement system may comprise a temperature reading apparatus 1026d, an optional agitator 1090 for mixing the liquid, as well as, at least one level sensor 1050.

In embodiments, the volume measurement and density calibration system 1030 may comprise an inline refractometer 1024b operatively coupled to the chamber 1114 of the tank 1110.

Still referring to FIG. 3, in embodiments, it will be appreciated that the sap or the liquid may be directed volume measurement and density calibration system 1030 to a storing container or reservoir 2010 for storage or alternative, the sap or the liquid may be directed from volume measurement and density calibration system 1030 to the Brix measurement system 1000 for further analysis and measurements.

It will be appreciated, in embodiments as shown in FIG. 3, the method and system for measuring the Brix of maple sap in continuous (real time) or not 3001 may comprise one or more storage tanks 2020 for storing the sap, taffy or liquid.

Still referring to FIG. 3, in embodiments, from volume measurement and density calibration system 1030 or at least one of the storage tanks 2020 may comprise a heating device (2030a, 2030b) for regulating the temperature of the sap, taffy or liquid.

As it will be appreciated, still referring to FIG. 3, there is provided a cleaning system 2040 comprising a plurality of tanks (2042, 2044) allowing a cleaning liquid to circulate and be recirculated to clean system for measuring the Brix of maple sap in continuous (real time) or not 3001. The cleaning liquid may be a cleaning acid used in the food industry, preferably, citric acid.

In embodiments, as provided in FIG. 3, the method and system for measuring the Brix of maple sap in continuous (real time) or not 3001 may be fluidly coupled to a plurality intervening devices such as pumps (2050a, 2050b, 2050c, 2050d) to facilitate the transport of sap or liquid through the different systems and/or for the cleaning of system for measuring the Brix of maple sap in continuous (real time) or not 3001.

The above description of the variants, examples or embodiments should not be interpreted in a limiting manner since other variations, modifications and refinements are possible within the scope of the present invention. Accordingly, it should be understood that various features and aspects of the disclosed variants or embodiments can be combined with or substituted for one another in order to form varying modes of the disclosed invention. For example, and without limitation, any individual element of the described variants or embodiments may be replaced by alternative elements that provide substantially similar functionality or otherwise provide adequate operation. This includes, for example, presently known alternative elements, such as those that might be currently known to a skilled person in the art, and alternative elements that may be developed in the future, such as those that a skilled person in the art might, upon development, recognize as an alternative. The scope is defined in the appended claims and their equivalents.

The invention claimed is:

1. A system for measuring a Brix of a liquid, the system comprising: —a tank for receiving therein a volume of the liquid; —an inlet opening fluidly connected to the tank for conveying the liquid into the tank; —an outlet opening fluidly connected to the tank for expelling the liquid from the tank; —a temperature reading apparatus for measuring a temperature of the liquid; —a weighing apparatus for measuring a weight of the volume of liquid received in the tank; —a volume measurement system for measuring the volume of the liquid received in the tank; and —a computer operatively connected to the temperature reading apparatus, the weighing apparatus and the volume measurement system and receiving data from the temperature reading apparatus, the weighing apparatus and the volume measurement system, the computer being programmed to determine a Brix measurement based on the data received from the temperature reading apparatus, the weighing apparatus and the volume measurement system.

2. The system of claim 1, wherein the temperature of the liquid is measured prior to entering the tank, in the tank or after being expelled from the tank.

3. The system of claim 1, wherein the computer is programmed with an algorithm correlating a Brix value of the liquid received in the tank based on the volume, the weight and the temperature of the liquid received in the tank to determine the Brix measurement of the liquid received in the tank.

4. The system of claim 1, wherein the temperature reading apparatus comprises one temperature sensor.

5. The system of claim 4, wherein the at least one temperature sensor is selected from a group consisting of a thermometer, a negative temperature coefficient (NTC), thermistor, a resistance temperature detector (RTD), a semiconductor-based sensor, an infrared sensor and a bimetallic device.

6. The system of claim 1, further comprising:
an inlet pipe fluidly connected to the inlet opening for conveying the liquid into the tank;
an outlet pipe fluidly connected to the outlet opening for tank for expelling the liquid from the tank;
and wherein the temperature reading apparatus is mounted to at least one of the tank, the inlet pipe and the outlet pipe.

7. The system of claim 6, wherein the temperature reading apparatus comprises one temperature sensor mounted to one of: the tank, the inlet pipe and the outlet pipe.

8. The system of claim 7, wherein the temperature reading apparatus comprises a first temperature sensor mounted to the tank, a second temperature sensor mounted to the inlet pipe and a third temperature sensor mounted to the outlet pipe.

9. The system of claim 1, wherein the weighing apparatus comprises one load cell operatively associated with the tank for measuring the weight of the volume of liquid received in the tank.

10. The system of claim 9, wherein the at least one load cell is supported on a floor surface, and the tank is supported onto the load cell.

11. The system of claim 9, wherein the at least one load cell is suspended to a ceiling structure and the tank is suspended by the load cell.

12. The system of claim 1, wherein the tank has a defined maximum volume, the volume measurement system being configured for filling the tank with the liquid to the defined maximum volume.

13. The system of claim 1, wherein the volume measurement system further comprises gas removing means associated with the tank for removing gas present in the liquid contained in the tank.

14. The system of claim 1, wherein the volume measurement system comprises at least one level sensor operatively associated with the tank, the computer being configured for receiving data from the level sensor and extrapolating a volume of liquid contained in the tank for predetermined levels.

15. The system of claim 1, further comprising a Brix reading apparatus for measuring the Brix of the liquid prior to entering the tank, while received in the tank or after being expelled from the tank, the computer being operatively connected to the Brix reading apparatus and receiving data from the the Brix reading apparatus, the computer being programmed to account for the data received from the Brix reading apparatus to determine the Brix measurement.

16. The system of claim 15 wherein the Brix reading apparatus comprises a refractometer.

17. The system of claim 1, wherein the liquid is selected from a group consisting of sap and syrup.

18. The system of claim 17, wherein the sap comprises maple sap and the syrup comprises maple syrup.

19. A method form measuring Brix from a liquid, the method comprising;
Providing a system according to claim 1;
Measuring the temperature of the liquid received in the tank using the temperature reading apparatus;
Measuring the weight of the liquid received in the tank using the weighing apparatus;
Measuring the volume of the liquid received in the tank using the volume measurement system;
Receiving data from the temperature reading apparatus, the weighing apparatus and the volume measurement system; and
Determining the Brix measurement based on the data received from the temperature reading apparatus, the weighing apparatus and the volume measurement system using the computer.

* * * * *